US010940461B2

(12) United States Patent
Gao et al.

(10) Patent No.: US 10,940,461 B2
(45) Date of Patent: *Mar. 9, 2021

(54) AGGLOMERATED ODH CATALYST

(71) Applicant: NOVA Chemicals (International) S.A., Fribourg (CH)

(72) Inventors: Xiaoliang Gao, Calgary (CA); Marie Annette Barnes, Calgary (CA); Yoonhee Kim, Calgary (CA); Vasily Simanzhenkov, Calgary (CA); David Sullivan, Calgary (CA); Renee Laurel Anseeuw, Calgary (CA); Yipei Styles, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 11 days.

This patent is subject to a terminal disclaimer.

(21) Appl. No.: 16/040,987

(22) Filed: Jul. 20, 2018

(65) Prior Publication Data
US 2019/0039050 A1 Feb. 7, 2019

(30) Foreign Application Priority Data

Aug. 3, 2017 (CA) ........................ 2975140

(51) Int. Cl.
*B01J 23/20* (2006.01)
*B01J 23/28* (2006.01)
(Continued)

(52) U.S. Cl.
CPC .............. *B01J 23/20* (2013.01); *B01J 21/04* (2013.01); *B01J 21/063* (2013.01); *B01J 21/066* (2013.01); *B01J 23/002* (2013.01); *B01J 23/28* (2013.01); *B01J 27/0576* (2013.01); *B01J 35/023* (2013.01); *B01J 35/08* (2013.01); *B01J 35/108* (2013.01); *B01J 35/1009* (2013.01);
(Continued)

(58) Field of Classification Search
CPC .. B01J 23/002; B01J 2523/55; B01J 2523/56; B01J 2523/64; B01J 2523/68; B01J 27/0576; B01J 21/04; C07C 2523/20; C07C 2523/22; C07C 2527/057
See application file for complete search history.

(56) References Cited

U.S. PATENT DOCUMENTS 4,524,236 A 6/1985 McCain
6,180,825 B1 * 1/2001 Lin ....................... B01J 23/002
502/241
(Continued)

FOREIGN PATENT DOCUMENTS

EP 0 262 264 A1 4/1988

OTHER PUBLICATIONS

Zhao et al., Comparative study of bulk and supported V—Mo—Te—Nb—O mixed meal oxide catalyst for oxidative dehydrogenation of propane to propylene, J. Phys. Chem. B., 2003, vol. 107, p. 6333-6342.*

(Continued)

*Primary Examiner* — Jun Li
(74) *Attorney, Agent, or Firm* — Thomas J. Styslinger

(57) ABSTRACT

Oxidative dehydrogenation catalysts for converting lower paraffins to alkenes such as ethane to ethylene when prepared as an agglomeration, for example extruded with supports comprising slurries of $Nb_2O_5$.

20 Claims, 10 Drawing Sheets

(51) Int. Cl.
*B01J 27/02* (2006.01)
*B01J 35/10* (2006.01)
*B01J 37/08* (2006.01)
*B01J 23/16* (2006.01)
*C07C 5/48* (2006.01)
*B01J 37/04* (2006.01)
*B01J 37/10* (2006.01)
*B01J 37/03* (2006.01)
*B01J 37/06* (2006.01)
*B01J 27/057* (2006.01)
*B01J 21/04* (2006.01)
*B01J 21/06* (2006.01)
*B01J 23/00* (2006.01)
*B01J 35/02* (2006.01)
*B01J 35/08* (2006.01)
*B01J 37/00* (2006.01)
*C07C 5/333* (2006.01)

(52) U.S. Cl.
CPC ....... *B01J 35/1038* (2013.01); *B01J 37/0009* (2013.01); *B01J 37/03* (2013.01); *B01J 37/04* (2013.01); *B01J 37/06* (2013.01); *B01J 37/08* (2013.01); *B01J 37/10* (2013.01); *C07C 5/3332* (2013.01); *C07C 5/48* (2013.01); *B01J 2523/00* (2013.01); *B01J 2523/55* (2013.01); *B01J 2523/56* (2013.01); *B01J 2523/64* (2013.01); *B01J 2523/68* (2013.01); *C07C 2523/20* (2013.01); *C07C 2523/22* (2013.01); *C07C 2523/28* (2013.01); *C07C 2527/057* (2013.01)

(56) References Cited

U.S. PATENT DOCUMENTS

| | | | |
|---|---|---|---|
| 7,319,179 | B2 | 1/2008 | Lopez Nieto et al. |
| 8,846,996 | B2 | 9/2014 | Kustov et al. |
| 8,962,517 | B2 | 2/2015 | Zurcher et al. |
| 2003/0065235 | A1* | 4/2003 | Allison .............. B01J 23/10 |
| | | | 585/656 |
| 2010/0256432 | A1* | 10/2010 | Arnold .............. C07C 5/48 |
| | | | 585/655 |
| 2014/0121433 | A1 | 5/2014 | Cizeron et al. |
| 2014/0194642 | A1* | 7/2014 | Endo ............... B01J 27/0576 |
| | | | 558/330 |
| 2014/0249339 | A1* | 9/2014 | Simanzhenkov ..... C07C 5/48 |
| | | | 585/252 |
| 2015/0141727 | A1 | 5/2015 | Simanzhenkov et al. |
| 2017/0008821 | A1 | 1/2017 | Hossain et al. |
| 2017/0050178 | A1* | 2/2017 | Simanzhenkov ..... C07C 5/48 |
| 2017/0137348 | A1* | 5/2017 | Schoonebeek ..... B01J 35/023 |
| 2017/0233312 | A1* | 8/2017 | Hossain .............. C07C 5/42 |
| | | | 585/656 |

OTHER PUBLICATIONS

Yu et al., Nonacrystalline mixed oxides for the selecticve oxidation of propane, International Conference on Materials Chemistry and Envrionmental Protection, MEEP 2015, 0040-0042.*

Bortella, P.; Garcia-Gonzalez, E.; Dejoz, A.; Lopez Nieto, J.M.; Vazquez, M.I. and Gonzalez-Galbet, J.; Selective oxidative dehydrogenation of ethand on MoVTeNbO mixed metal oxide catalysts; Copyright 2004; Journal of Catalysis 225, pp. 428-438.

* cited by examiner

Baseline ODH catalyst with 60% Nb$_2$O$_5$

Relationship between the percent pore area and the percent of loaded Nb₂O₅ in the agglomerated catalyst
Pore Are vs. Nb₂O₅ loading for ODH catalysts Relationship between Pore Area (%) and Activity of agglomerated catalyst at 25% conversion

AGGLOMERATED ODH CATALYST

The present disclosure relates to agglomerated oxidative dehydrogenation catalysts to convert paraffins, for example $C_{2-4}$, or for example ethane, to the corresponding alkene. Such reactions may take place in fixed bed or fluidized bed reactors. There is a need to form catalyst particles having sufficient strength to avoid attrition during use. $Nb_2O_5$ hydrate is useful as a binder for the catalyst particles. At lower levels of $Nb_2O_5$ hydrate as a binder component the activity of the catalyst in terms of temperature at which 25% conversion is obtained may be improved without significant (e.g., less than 5%) reduction in selectivity.

U.S. Pat. No. 4,524,236 issued Jun. 18, 1985 to McCain assigned to Union Carbide Corporation teaches a catalyst for the oxidative dehydrogenation of ethane to ethylene comprising a calcined composition of $Mo_a$ $V_b$ $Nb_c$ $Sb_d$ $X_e$ wherein:

X=at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W; and
a=0.5 to 0.9
b=0.1 to 0.4
c=0.001 to 0.2
d=0.001 to 0.1.
e=0.001 to 1.0

The values of a, b, c, d and e constitute relative gram-atoms of the elements Mo, V, Nb, Sb, and X respectively, in the catalyst. The elements are present in combination with oxygen in a form of various oxides.

The patent teaches the catalyst may be used with or without a support. The catalyst is prepared as a solution and dried and calcined. The patent teaches suitable supports for the catalyst include silica, aluminum oxide, silicon carbide, zirconia, titania, and mixtures thereof. When used on a support, the supported catalyst usually comprises from about 10 to 50% by weight of the catalyst composition, with the remainder being the support. The patent teaches the support is impregnated with the catalyst (Col. 4 lines 38 to 43). The patent fails to teach $Nb_2O_5$ as a support (or promotor) for an oxidative dehydrogenation catalyst.

European Patent Application No. 0 262 264 (corresponds to CA 1262556) published Mar. 30, 1988 in the name of Manyik et al., assigned to Union Carbide Corporation teaches a process to dehydrogenate ethane to ethylene using the catalyst of U.S. Pat. No. 4,524,236 issued Jun. 18, 1985 to McCain. The patent application teaches the catalyst solution is used to impregnate (i.e. an incipient wetness method) a support (page 7 lines 30-35). The supports have a surface area of less than about 1 square meter per gram and a relatively large median pore diameter of greater than 10 microns. The patent does not teach an agglomerated catalyst. The incipient wetness impregnations require the use of a solution of dissolved catalyst with a controlled type (improve adsorption into the pores) and volume of solvent to minimally wet the support. The pore size, the composition of the support (hydrophobic or hydrophilic) and type and amount of solvent place constraints on the up take and placement of active catalyst within the supported catalyst. An agglomeration method is conducted by blending dispersions of binder and support with optional reduction of solvent/diluent, extrusion and final drying. The agglomeration process gives a wider window for ratios of binder to catalyst and also provides enhanced control over pore volume, size and distribution. The patent fails to teach $Nb_2O_5$ as a support for an oxidative dehydrogenation catalyst.

U.S. Pat. No. 7,319,179 issued Jan. 15, 2008 to Lopez Nieto et al., assigned to Conseio Superior de Investigacionse Cientificas and Universidad Politecnica De Valencia teaches a five component metal oxide catalyst for the oxidative dehydrogenation of ethane. The patent teaches the catalyst can be a mixed oxide supported on a solid, such as for example silica, alumina, titanium oxide and mixtures thereof. In some embodiments, the silica as solid support is present in proportion of 20 to 70% by weight with respect to the total weight of catalyst. Moreover, the catalyst can also be in the form of a mixed oxide supported on a silicon carbide. The fixing of the different elements of the catalyst on the support can be done by conventional methods of impregnation, such as pore volume, excess solution, or simply by precipitation on the support of a solution containing the active elements. The patent seems to be teaching to individually bind each element of the catalyst on the support. The patent fails to teach $Nb_2O_5$ as a support for an oxidative dehydrogenation catalyst.

U.S. Published Application No. 20140121433 published May 1, 2014 in the name of Cizeron et al., assigned to Siluria teaches catalysts for oxidative coupling of methane. The disclosure seems to use the terms binder and diluent interchangeable. The oxidative coupling catalyst for methane (OCM) is a nanowire. The patent also teaches catalyst which may be used for oxidative dehydrogenation of ethane [357 and 358]. The passages at paragraphs [0146 through [0153] discuss "diluents". These appear to be inert. The patent application fails to teach $Nb_2O_5$ as a support for an oxidative dehydrogenation catalyst.

U.S. Pat. No. 8,846,996 issued Sep. 30, 2014 in the name of Kustov et al., assigned to NOVA Chemicals (International) S.A. teaches co-comminution (wet or dry milling Col 5 line 50) of an oxidative dehydrogenation catalyst with an inert support selected from the group oxides of titanium, zirconium, aluminum, magnesium, yttrium, lanthanum, silicon and their mixed compositions or a carbon matrix, to produce particles having a size from 1 to 100 microns and forming the resulting particles into pellets having a size from 0.1 to 2 mm. The present disclosure has done away with the co-comminution step. Additionally the product of the co-comminution step is formed into pellets and crushed to obtain the right particle size (Col. 5 line 55). The patent fails to teach $Nb_2O_5$ as a support for an oxidative dehydrogenation catalyst.

U.S. Published Application No. 20170008821 published Jan. 12, 2017 in the name of Hossain et al., assigned to King Fand University of Petroleum and Minerals teaches an oxidative dehydrogenation process conducted in the absence of gaseous oxygen conducted in a circulating stirred bed reactor. The catalyst comprises lattice oxygen. When the oxygen is depleted from the catalyst it is circulated to an oxidation reactor where the lattice oxygen is replenished. The catalyst is supported on an alumina based support which has been treated with $ZrO_2$ using an incipient wetness process (paragraph 64). The catalyst is then supported on the treated support also using an incipient wetness process. The catalyst is not prepared using an extrusion method. The patent fails to teach $Nb_2O_5$ as a support for an oxidative dehydrogenation catalyst.

There are some patents which disclose the use of Nb as a promoter for lanthanide catalysts for the oxidative dehydrogenation or oxidative coupling of lower alkanes. One examples of this is U.S. Pat. No. 8,962,517 issued Feb. 24, 2015 to Zucher et al., assigned to Siluria, which suggests using Nb as a promoter for lanthanide oxide catalysts. The patent does not appear to teach metal oxide catalysts as disclosed herein and does not suggest that $Nb_2O_5$ could be useful as a binder with such catalysts.

The present disclosure seeks to provide an (extruded) agglomerated catalyst for the oxidative dehydrogenation of ethane which may be extruded into various shapes having improved activity. The catalysts are extruded onto acid, neutral or basic supports comprising $Nb_2O_5$.

Provided herein are agglomerated, or for example, extruded, catalysts comprising:

i) 10 to 95 weight % of a catalyst active phase of the formula: $Mo_{1.0}V_{0.12-0.49}Te_{0.6-0.16}Nb_{0.15-0.20}O_d$ wherein d is a number to satisfy the valence of the oxide;

ii) from 5 to 90 weight % of $Nb_2O_5$; and iii) optionally up to 80 wt % of a non-antagonistic binder or support.

In a further embodiment, the agglomerated catalyst has a cumulative surface area less than 10 m$^2$/g as measured by BET, alternatively, less than 8 m$^2$/g, alternatively, less than 5 m$^2$/g.

In a further embodiment, the agglomerated catalyst has a cumulative pore volume from 0.02 to 0.20 cm3/g.

In a further embodiment, the agglomerated catalyst has a pore size distribution so that less than 40% of the pores have a pore width size less than 200 Angstroms (e.g. 60% of the pores have a size greater than 200 A).

In a further embodiment, the agglomerated catalyst has a percent pore area distribution less than 30% and corresponding percentage of pore volume less than 10%.

In a further embodiment, the agglomerated catalyst is in the shape of a sphere, rod, ring, or a saddle having a size from about 1.3 mm to 5 mm.

In a further embodiment, the $Nb_2O_5$ hydrate is acidified.

In a further embodiment, the $Nb_2O_5$ hydrate is treated with a base.

In a further embodiment, the agglomerated catalyst is in the shape of rods having an aspect ratio from 1 to 5/1.3 having a crush strength up to 110 N/mm.

In a further embodiment, the agglomerated catalyst is in the shape of spheres having a crush strength up to 110 N.

In a further embodiment, the $Nb_2O_5$ hydrate is present in an amount less than 15 wt %.

In a further embodiment, the $Nb_2O_5$ hydrate is present in an amount greater than 15 wt %.

In a further embodiment, in the agglomerated catalyst, the catalyst active phase has the empirical formula:

$$Mo_{1.0}V_{0.25-038}Te_{0.10-0.16}Nb_{0.15-0.19}O_d$$

where d is a number to satisfy the valence of the oxide.

In a further embodiment, in the agglomerated catalyst, the catalyst active phase has the empirical formula as measured by PIXE:

$$Mo_{1.0}V_{0.22-033}Te_{0.10-0.16}Nb_{0.15-0.19}O_d$$

where d is a number to satisfy the valence of the oxide.

In a further embodiment, in the agglomerated catalyst, the catalyst active phase has the empirical formula as measured by PIXE:

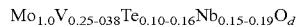

where d is a number to satisfy the valence of the oxide.

In a further embodiment, in the agglomerated catalyst, the catalyst active phase has the empirical formula as measured by PIXE:

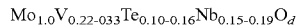

where d is a number to satisfy the valence of the oxide

In a further embodiment, in the agglomerated catalyst, the catalyst active phase has the empirical formula as measured by PIXE:

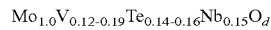

where d is a number to satisfy the valence of the oxide

In a further embodiment, there is provided a method to prepare a catalyst as above comprising:

i) forming an aqueous slurry or paste comprising up 10 to 95 wt. % of catalyst active phase;

ii) adding to the slurry or paste up to 5 to 90 wt % on of a binder of $Nb_2O_5$ hydrate in the form of an acidic, neutral or basic colloidal suspension having a pH up to 12, in some embodiments from 1-12;

iii) optionally up to 80 wt % of a non-antagonistic binder;

iv) where required reducing the water content of the resulting slurry or paste to less than 30 wt %;

v) extruding the water reduced slurry or paste to form a, rod, ring or a saddle having a size from about 1.3 mm to 5 mm;

vi) drying the particles in an oxygen containing atmosphere at a temperature from 90° C. up to 115° C.; and vii) calcining the resulting particles at a temperature of up to 600° C.

In a further embodiment in step vi), the particles re calcined at a temperature of less than 350° C.

In a further embodiment, the rod shaped agglomerated particles are spheroidized at a temperature up to 300° C. and then further calcining the resulting spheres at temperatures up to 600° C.

The agglomerated catalyst as above wherein the non-antagonistic binder is chosen from oxides of aluminum, titanium and zirconium.

The agglomerated catalyst as above wherein the aluminum oxide is Boehmite (Al(O)OH).

The agglomerated catalyst as above wherein the non-antagonistic binder is an oxide of titanium.

The agglomerated catalyst as above wherein the non-antagonistic binder is an oxide of zirconium.

Further provided are methods for the oxidative dehydrogenation of a mixture comprising oxygen and one or more $C_{2-4}$ alkanes comprising passing the mixture over an extruded agglomerated catalyst as above, at a temperature from 340° C. to less than 420° C., a pressure from 172.3 kPag (25 psig) up to 689 kPag (100 psig), a space velocity from 500 hr$^{-1}$ to 3000 hr$^{-1}$, and a residence time from 0.002 to 20 seconds.

In a further embodiment, the oxidative dehydrogenation process comprising increasing the amount of binder in the extruded catalyst within the range of $Nb_2O_5$ binder in the catalyst in the range from 5 to 50 wt % and increasing the gas flow rate through the catalyst bed by a proportional amount while maintaining the bed temperature less than 420° C., or less than 395° C., or less than 385° C. and maintaining the selectivity within ±3%.

NUMBERS RANGES

Figure 1:
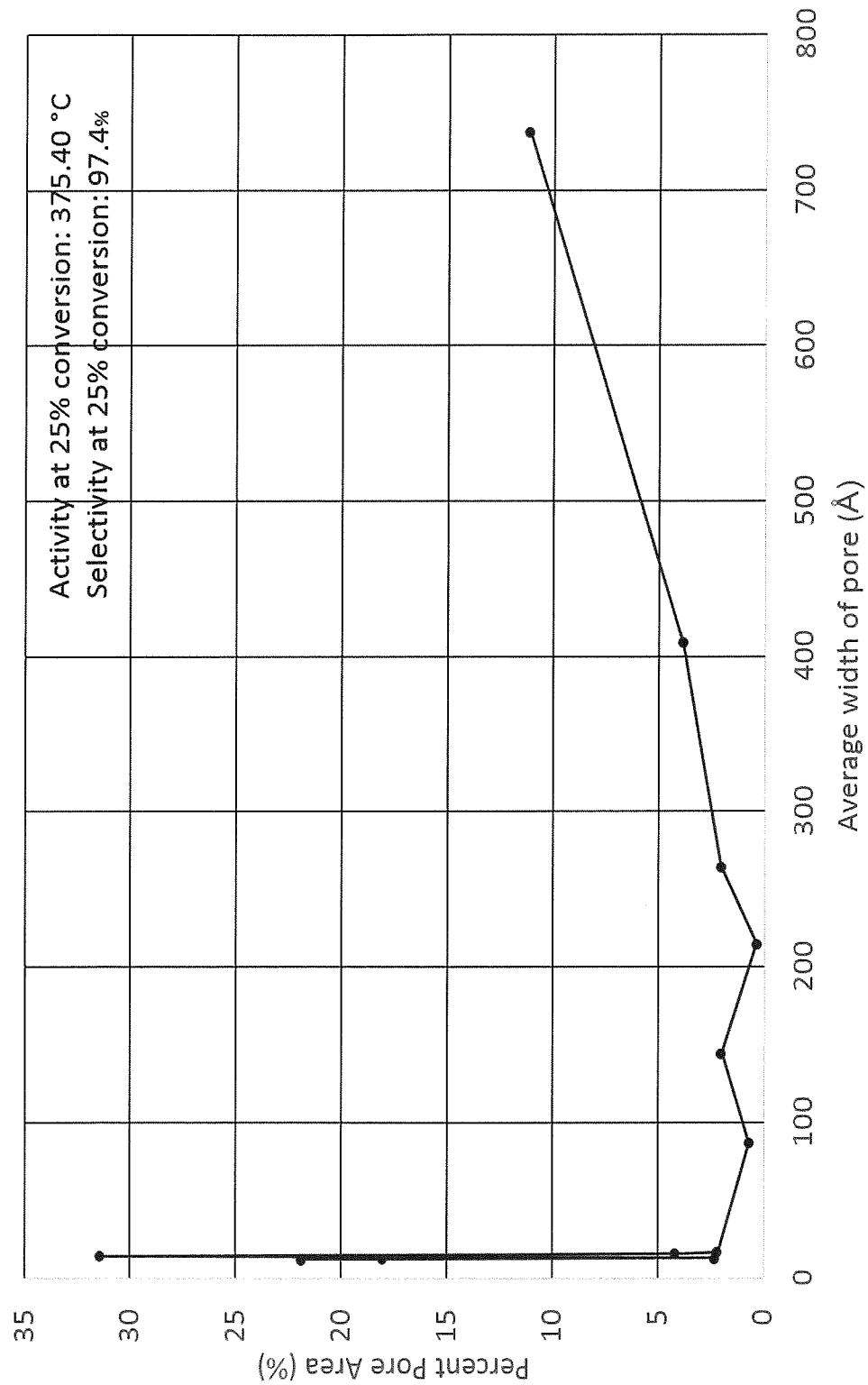
FIG. 1 is a plot of the percentage pore area of a catalyst with no binder as a function of pore width (sample 1) measured by BET (pore width distribution by percent pore area or percent volume).

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Binder means a material added to the catalyst to increase cohesion among the catalyst particles and optionally to improve adhesion of the catalyst to the support if present.

Promotor means a material added to the catalyst to lower the temperature at which 25% conversion of ethane was achieved with all other process conditions kept constant, thereby promoting the catalyst activity.

In the specification, the phrase "the temperature at which there is 25% conversion of ethane to ethylene" is determined by plotting a graph of conversion to ethylene against temperature typically with data points below and above 25% conversion or the data is fit to an equation and the temperature at which there is a 25% conversion of ethane to ethylene is determined. In some instances in the examples the data had to be extrapolated to determine the temperature at which 25% conversion occurred.

In the specification, the phrase "selectivity at 25% conversion" is determined by plotting the selectivity as function of temperature or fit to an equation. Then having calculated the temperature at which 25% conversion occurs one can determine either from the graph or from the equation the selectivity at that temperature.

In the specification, $Nb_2O_5$ refers to both the hydrated form of $Nb_2O_5$ (typically containing from about 18-25 wt % of water of hydration) when used as or in the form of an aqueous slurry, paste or dispersion or paste and also the dehydrated from of $Nb_2O_5$ when calcined in the agglomerated support. One skilled in the art will know or be able to determine which form $Nb_2O_5$ is being referred to or used.

In this specification, non-antagonistic binder means a binder other than $Nb_2O_5$ which when incorporated into the agglomerated catalyst has less than a 5% antagonistic effect on the agglomerated catalysts. Some non-antagonistic binders include oxides of aluminum, titanium and zirconium. Silica oxides have an antagonistic effect on the agglomerated catalysts and the catalyst active sites.

There are a number of ways to relate the surface area to the volume of gas, which can be incorporated into the agglomerated support.

One method is cumulative pore volume ($cm^3/g$) and cumulative surface area ($m^2/g$).

Figure 2:
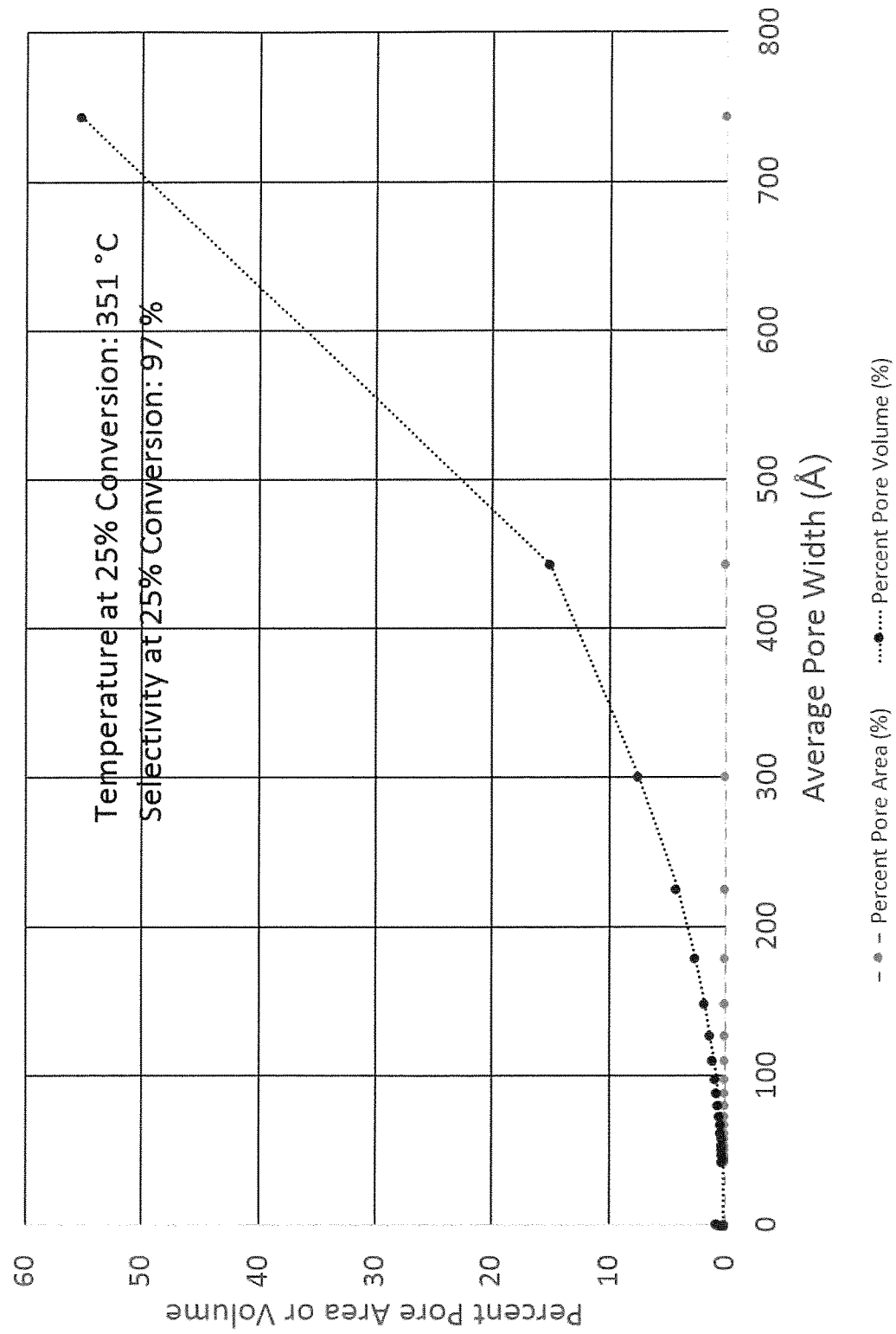
FIG. 2 is a plot of the percentage pore area overlaid with the percentage pore volume of a catalyst with 8 wt % $Nb_2O_5$ promotor as function of pore width (sample 11) measured by BET (pore width distribution by percent pore area or percent pore volume).
Figure 3:
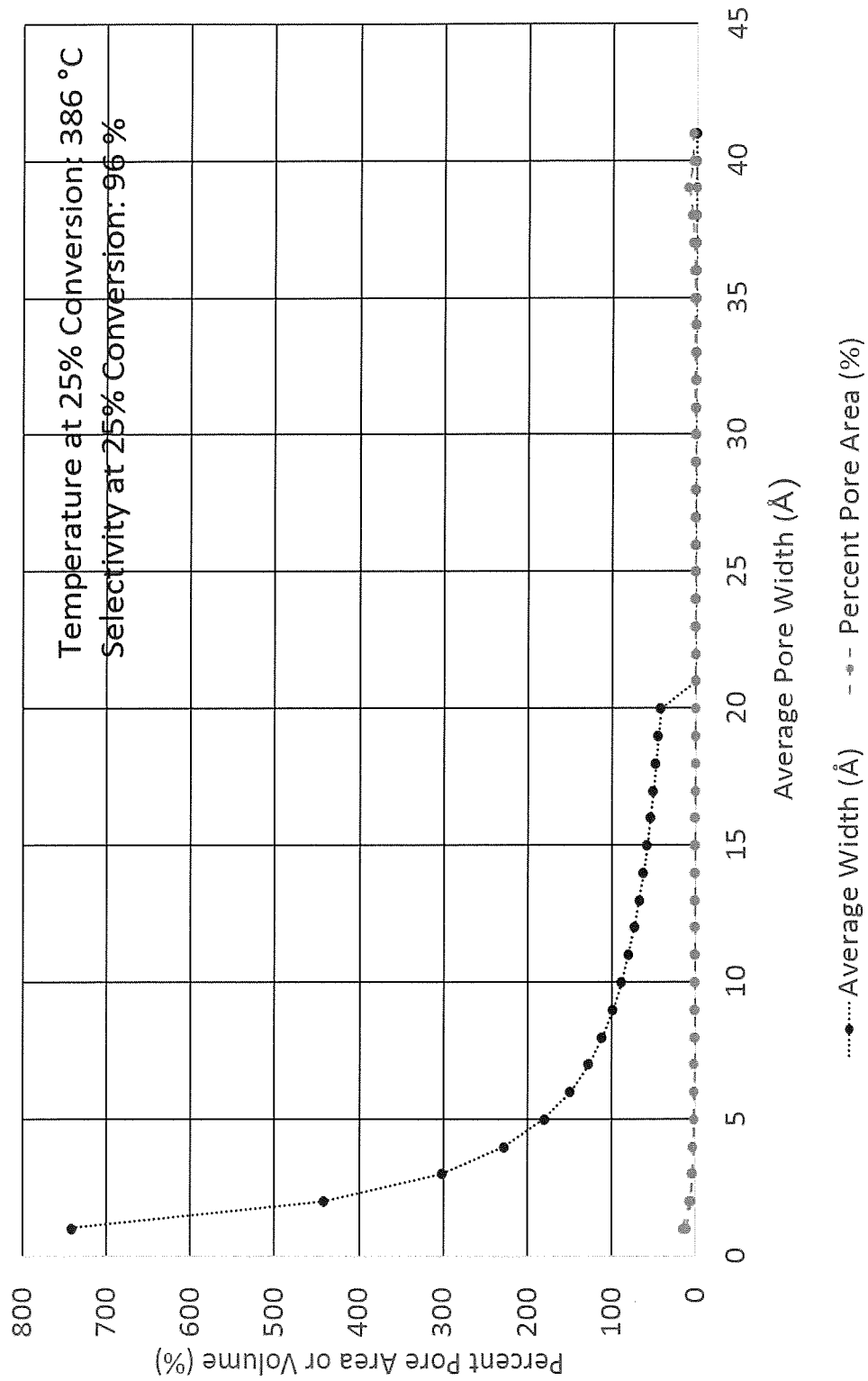
FIG. 3 is a plot of the percentage pore area overlaid with the percentage pore volume of of a catalyst with 15% $Nb_2O_5$ as a promotor as function of pore width (sample 7) measured by BET (pore width distribution by percent pore area or percent pore volume).
Figure 4:
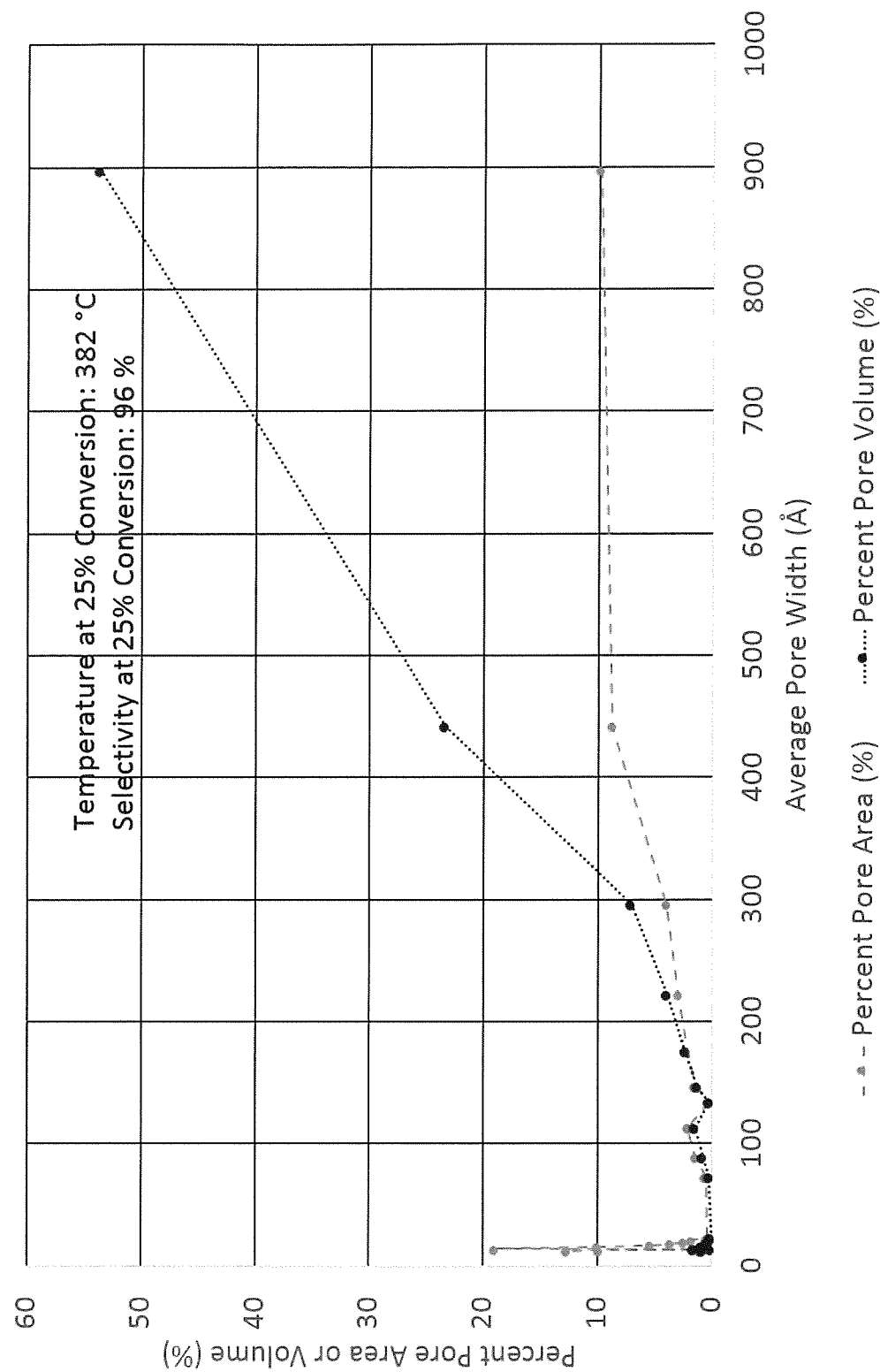
FIG. 4 is a plot of the percentage pore area overlaid with the percentage pore volume of of a catalyst with 20% $Nb_2O_5$ as a promotor as function of pore width (sample 8) measured by BET (pore width distribution by percent pore area or percent pore volume).
Figure 5:
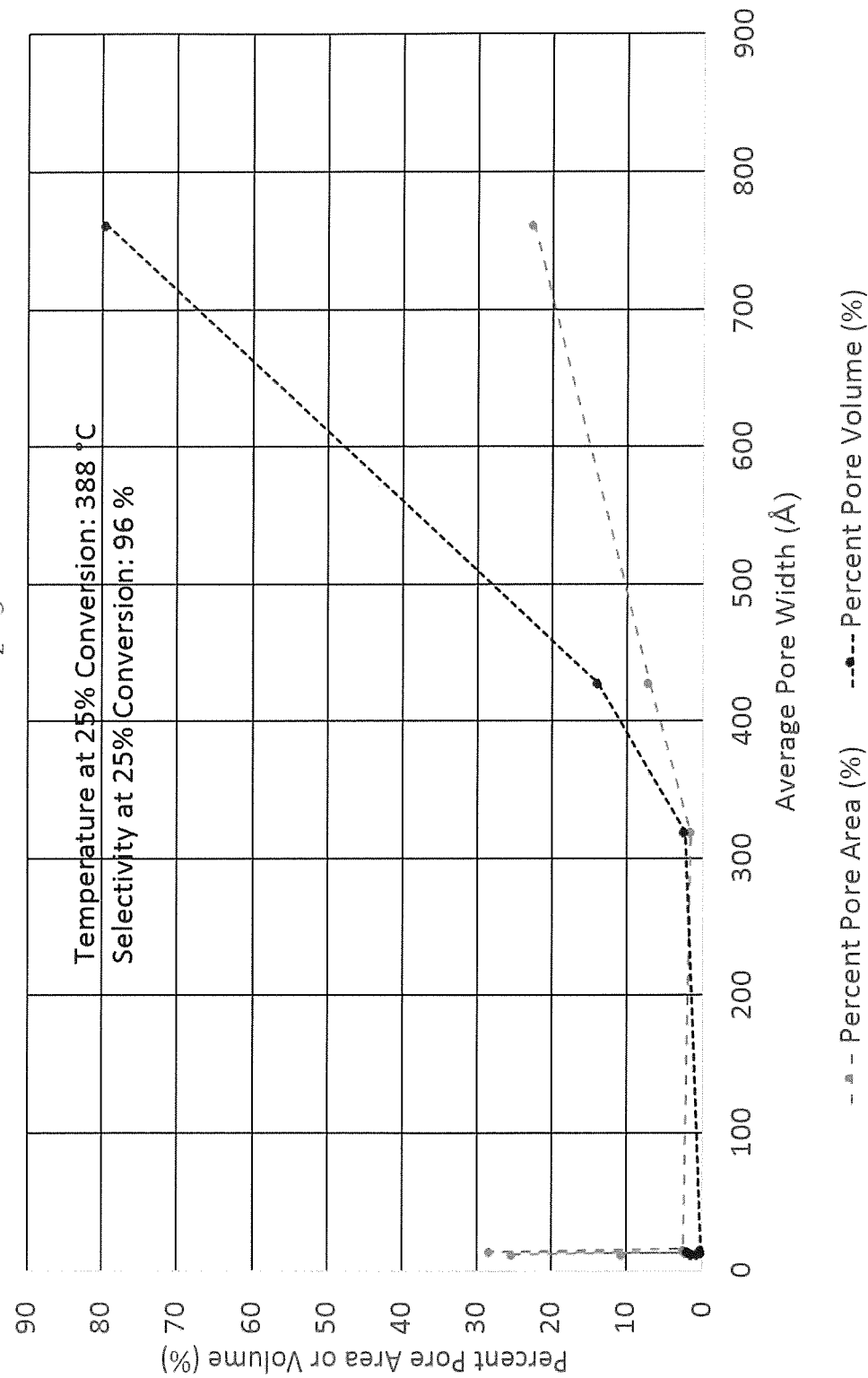
FIG. 5 is a plot of the percentage pore area overlaid with the percentage pore volume of of a catalyst with 40% $Nb_2O_5$ as a promotor as function of pore width (sample 9) measured by BET (pore width distribution by percent pore area or percent pore volume).
Figure 6:
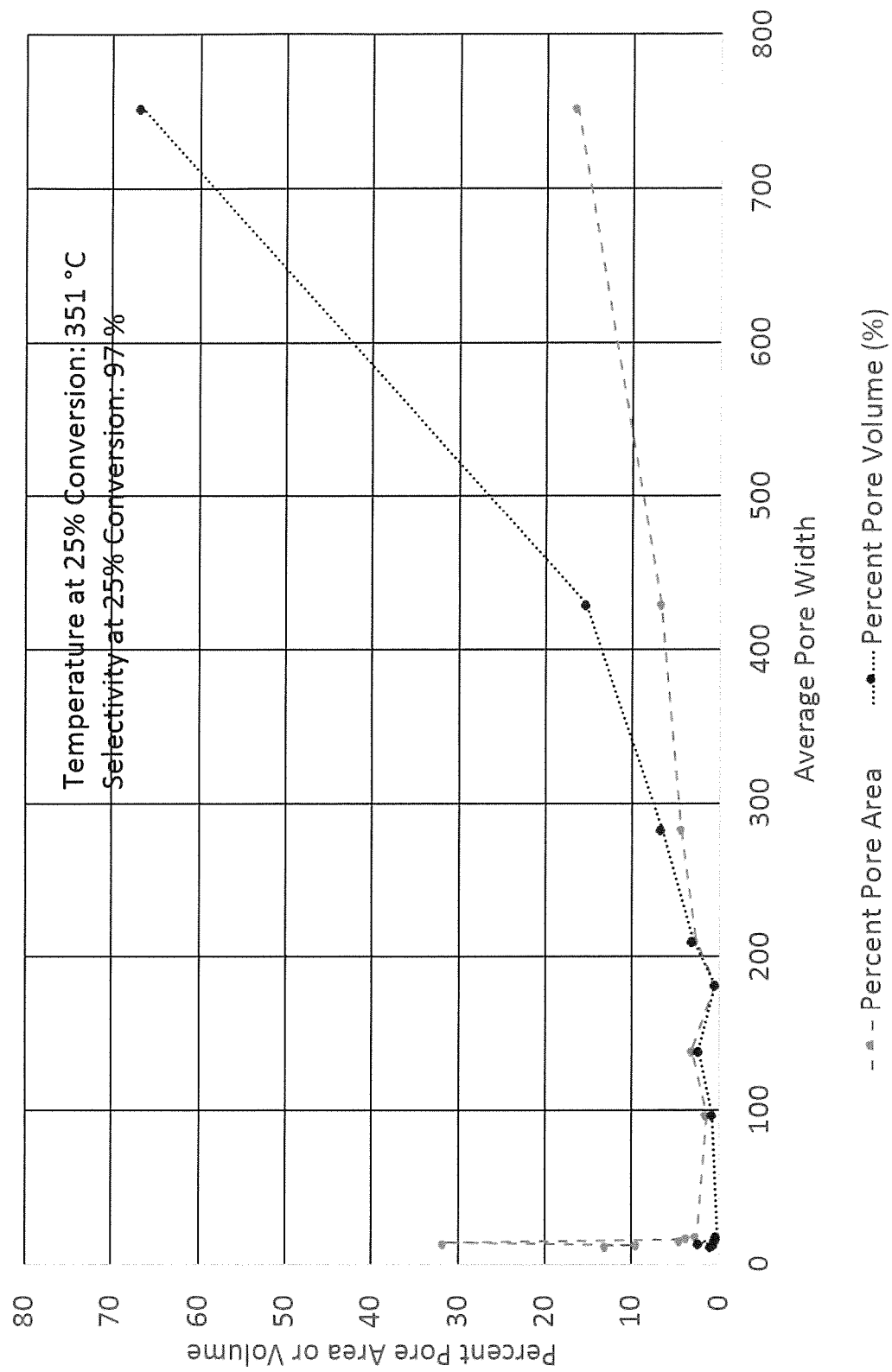
FIG. 6 is a plot of the percentage pore area overlaid with the percentage pore volume of a catalyst with 60% $Nb_2O_5$ as a promotor as function of pore width (sample 10) measured by BET (pore width distribution by percent pore area or percent pore volume).
Figure 7:
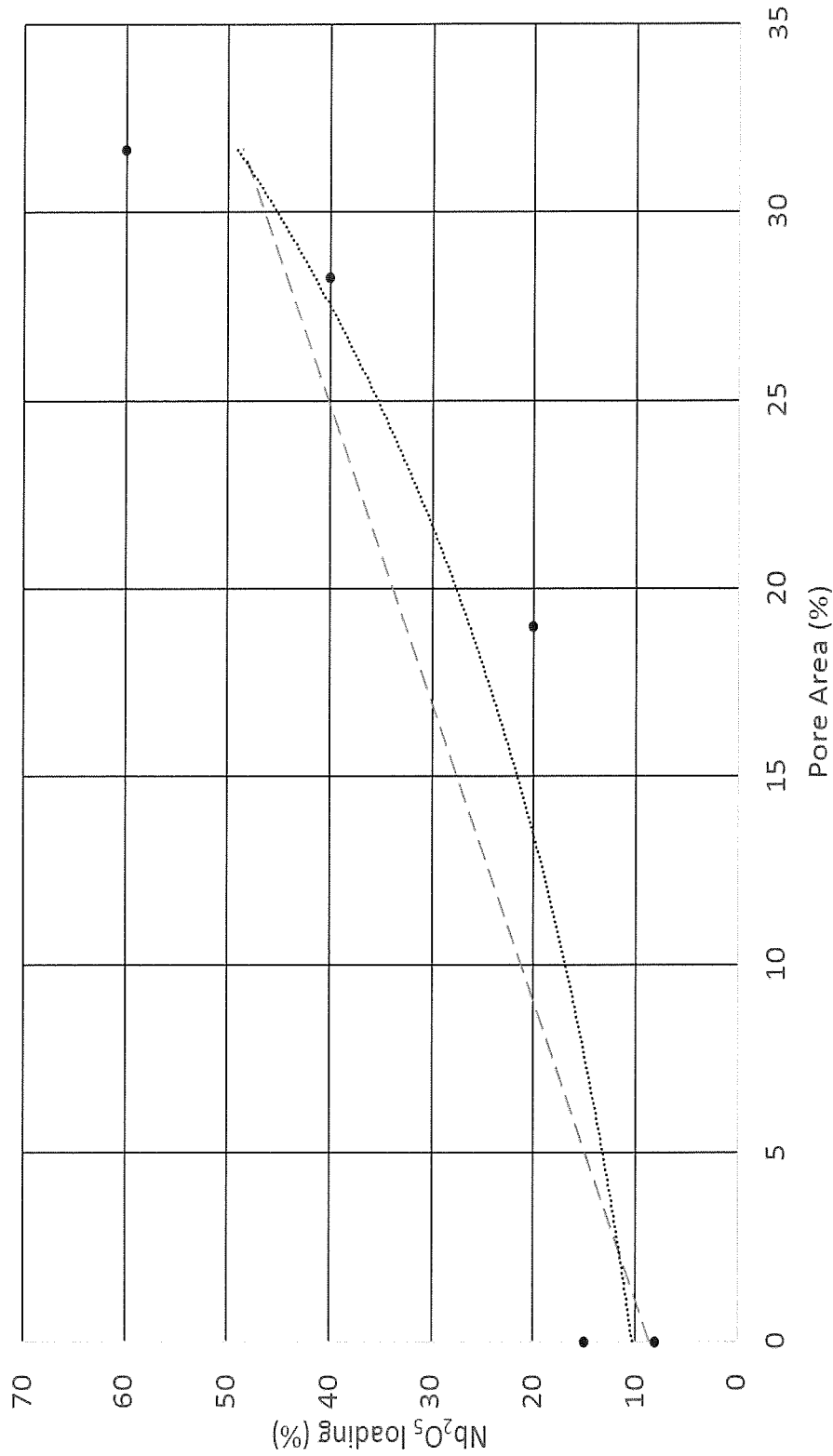
FIG. 7 Is a plot of the percent pore area as a function of the percent loading of $Nb_2O_5$.
Figure 8:
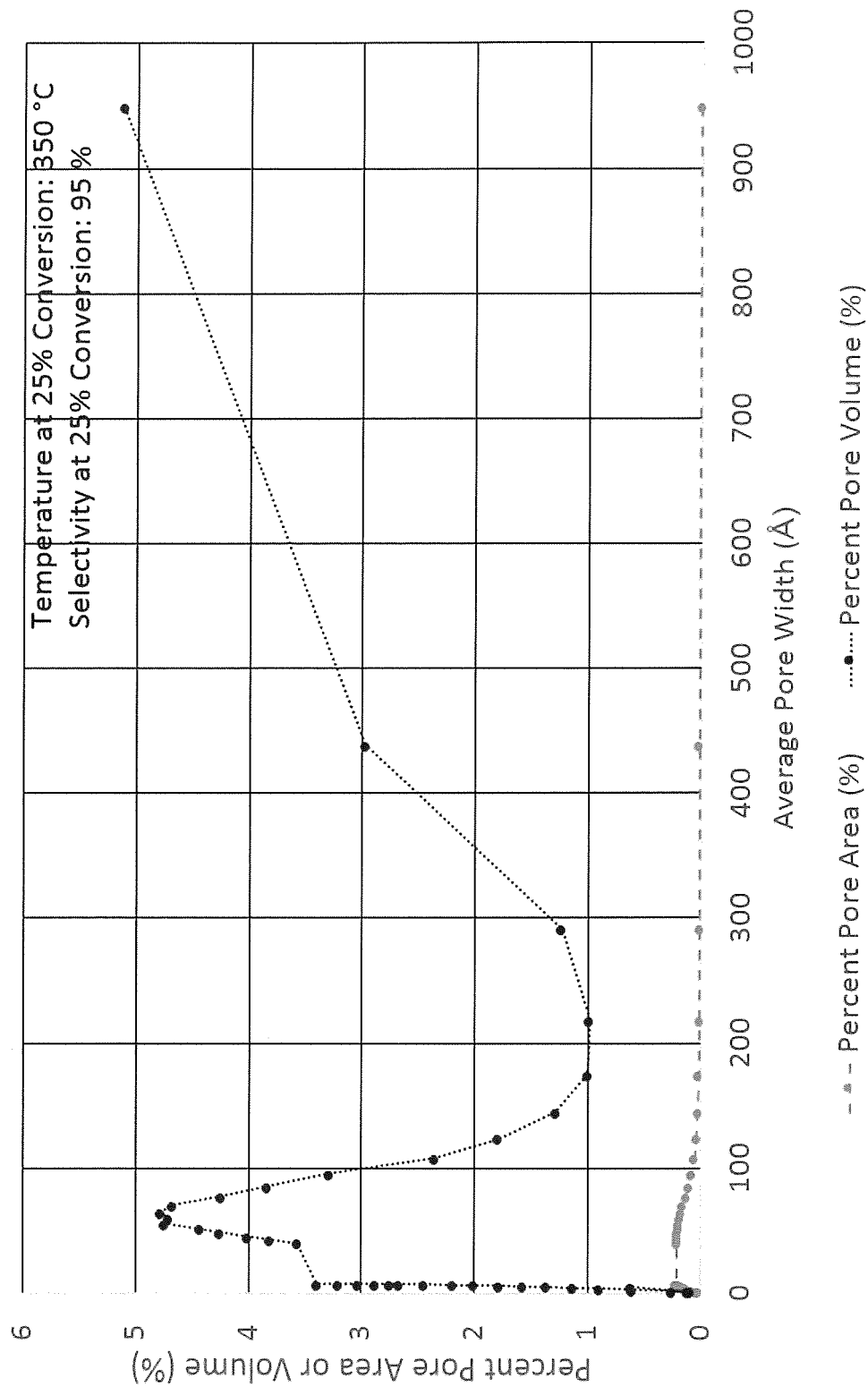
FIG. 8 is a plot of the percentage pore area overlaid with the percentage pore volume of of a catalyst with 8% $Nb_2O_5$ as a promotor and 60% of AlO(OH) as a binder as function of pore width (sample 12) measured by BET (pore width distribution by percent pore area or percent pore volume).
Figure 9:
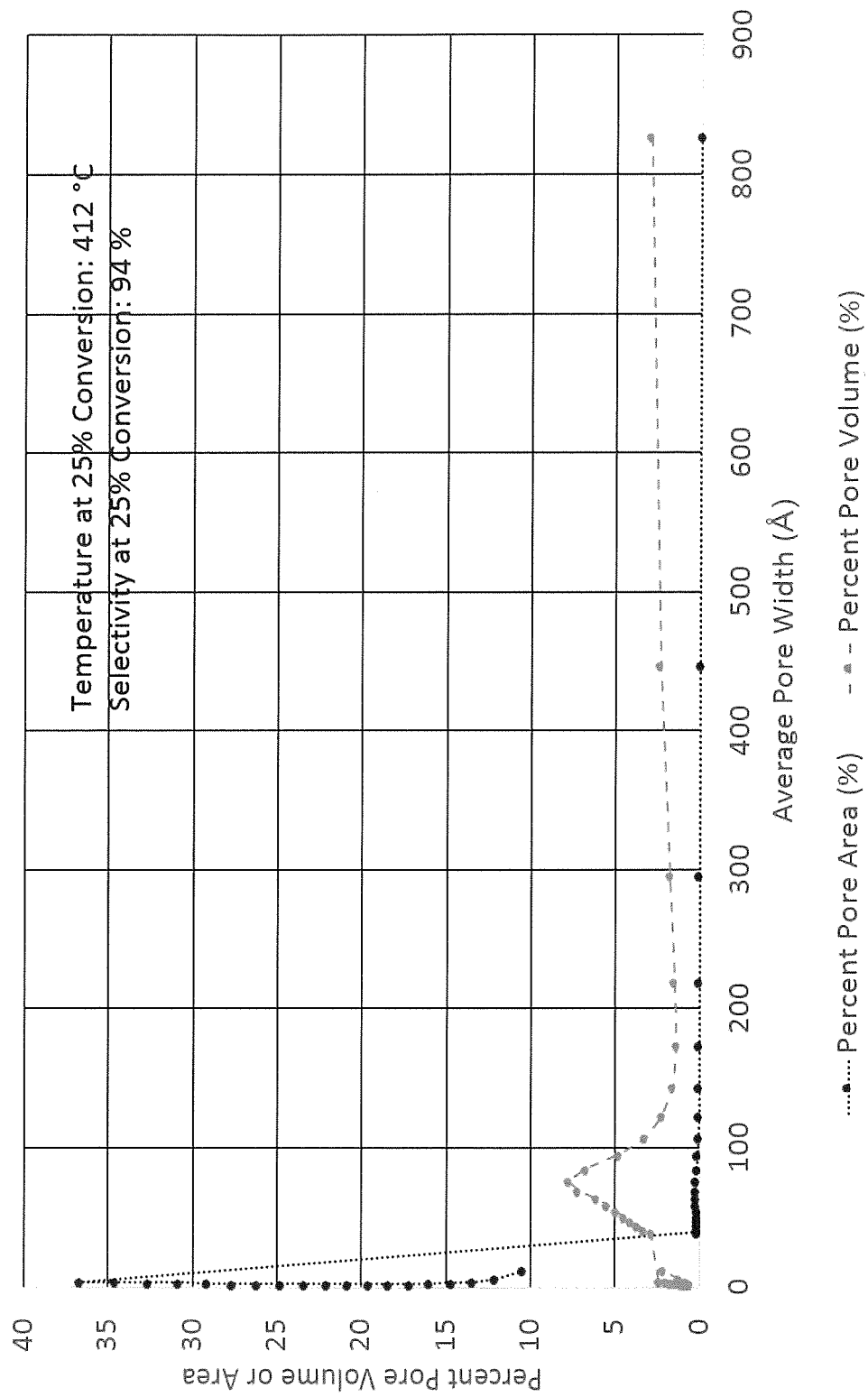
FIG. 9 is a plot of the percentage pore area overlaid with the percentage pore volume of of a catalyst with 8% $Nb_2O_5$ as a promotor and 60% $SiO_2$ as function of pore width (sample 13) measured by BET (pore width distribution by percent pore area or percent pore volume).
Figure 10:
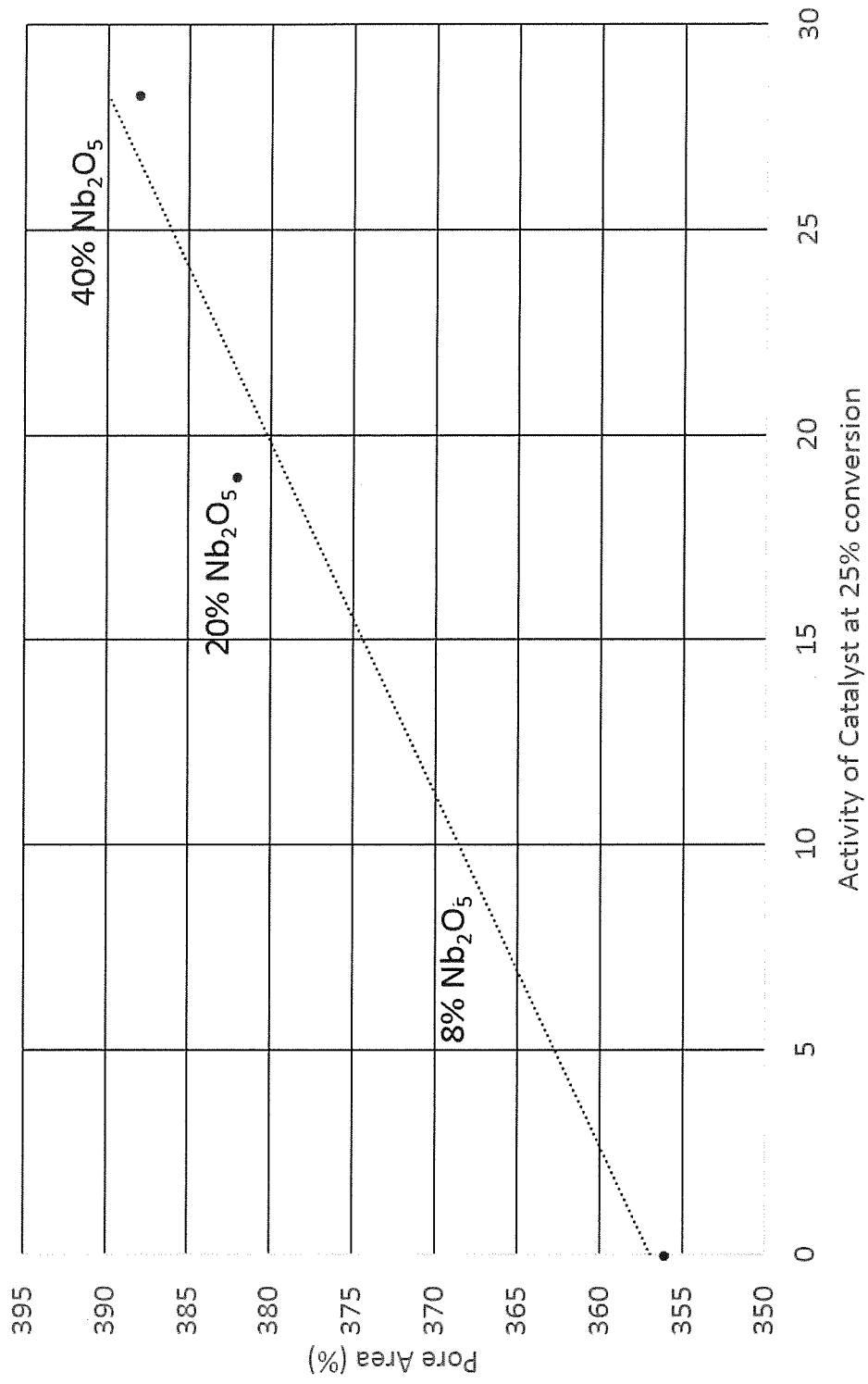
FIG. 10 is a plot of the percentage pore area as a function of activity of the catalyst at 25% conversion of ethane.

A second method is distribution of pore width to percentage of surface area. (for example, what surface area of the catalyst has a pore size of a defined diameter). In FIGS. 2 and 3, the catalyst $Nb_2O_5$ mixture has no defined pore area or pore volume associated with it. These figures represent $Nb_2O_5$ catalyst mixtures that contain 8-15% $Nb_2O_5$. In FIG. 5, 20% of the pore area has a range of pore width (diameter) of 17-22 Å. The remaining 80% of the pore area has a pore width (diameter) greater than 70 Å. In FIG. 6, 30% of the pore area has a range of pore width (diameter) of 12-16 Å. The remaining 70% of the pore area has a pore width (diameter) greater than 80 Å. In FIG. 7, 32% of the pore area has a range of pore width (diameter) of 12-14 Å. The remaining 68% of the pore area has a pore width (diameter) greater than 90 Å. In FIG. 8, lower loadings result in no pore structure, whereas higher loadings result in pore structures with increasing percent pore area with the increase in loading of the $Nb_2O_5$. The relationship is logarithmic or semi-logarithmic in nature. In FIG. 9, 5% of the pore area has a range of pore width (diameter) of 0-175 Å. The remaining 95% of pore area has a pore width greater than 175 Å. In FIG. 10, 36% of pore area has a range of pore width (diameter) of 5-40 Å. The remaining 64% of the pore area has a pore width (diameter) greater than 40 Å. In FIG. 11, higher percent pore area results in lower activities of the catalyst. Lower loadings have enhanced activities as compared to the baseline, whereas higher loadings have either no effect or reduced activities as compared to the baseline. Alumina and Silica both enhance the porosity with no effect on the activity and a negative effect on activity respectively.

The third method comprises:

first determining the cumulative surface area as function of cumulative pore volume;

secondly, normalize the cumulative surface area and cumulative pore volume to create percentages of the total distribution;

thirdly, plotting the surface area percentage as a function of pore volume percentage.

A fourth method exists and includes:

first determining the cumulative surface area as a function of cumulative pore volume;

secondly, normalize the cumulative surface area and cumulative pore volume to create percentages of the total distribution;

thirdly, plotting the surface area percentage as a function of percent loading of the $Nb_2O_5$ in the agglomerated catalyst. Alternatively, plotting the percent pore area as a function of activity of catalyst at 25% conversion.

For the oxidative dehydrogenation of lower ($C_{2-4}$) alkanes such as ethane the molecules being treated and the product molecules have a diameter from about 2.5-4 Angstroms (0.25-0.40 nm). The molecule diameter, the pore diameter and pore surface area influences the probability of the molecule interacting with a catalyst (on the pore wall or surface). For example large diameter pores, low inner surface area, and large pore volume would have the lowest probability of molecules making contact with the material inner surface (catalyst) resulting in a lower conversion.

One family of catalyst active phase useful in the oxidative dehydrogenation of lower alkanes such as $C_{2-4}$ alkanes and for example ethane to $C_{2-4}$ alkenes and for example ethylene are catalysts of mixed oxides of molybdenum, vanadium, tellurium, niobium and optionally other components such as Pt, Pd, Ta, Ti, W, Hf, Zr, Sb Zn, Sc, Y, La, Ce, Ta, Cr, W, U, Te, Fe, Co and Ni) for the oxidative dehydrogenation of ethane to ethylene.

One family of catalyst active phase useful for the oxidative dehydrogenation of alkanes, for example lower $C_{2-4}$ alkanes had the formula:

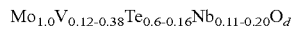

$Mo_{1.0}V_{0.12-0.38}Te_{0.6-0.16}Nb_{0.11-0.20}O_d$ wherein d is a number to satisfy the valence of the oxide.

The composition of the catalyst active phase may vary within the above generic formula depending on how the catalyst is manufactured.

Typically such catalysts and precursors, therefore, are made using a hydrothermal process.

Typically, in the hydrothermal process, the precursor for the catalyst active phase is prepared by:

i) forming an aqueous solution of ammonium heptamolybdate (tetrahydrate) and telluric acid at a temperature from 30° C. to 85° C. and adjusting the pH of the solution to from 6.5 to 8.5, or from 7 to 8, or from 7.3 to 7.7 with a nitrogen containing base to form soluble salts of the metals;

ii) preparing an aqueous solution of vanadyl sulphate at a temperature from room temperature to 80° C. (or for example from 50° C. to 70° C., or from 55° C. to 65° C.);

iii) mixing the solutions from steps i) and ii) together;

iv) slowly (dropwise) adding a solution of niobium monoxide oxalate ($NbO(C_2O_4H)_3$) to the solution of step iii) to form a slurry; and v) heating the resulting slurry in an autoclave under an inert atmosphere at a temperature from 150° C. to 190° C. for not less than 6 hours, in some instances not less than 10 h.

The resulting solid from step v) is filtered and washed with deionized water, and drying the washed solid for a time from 4 to 10 hours at a temperature from 70 to 100° C.

In a further embodiment, the precursor is calcined in an inert atmosphere at a temperature from 200° C. to 600° C. for a time from 1 to 20 hours.

The above is a typical hydrothermal process to prepare a precursor and final oxidative dehydrogenation catalyst active phase.

If the catalyst active phase is made using a conventional hydrothermal process it may have the formula:

$Mo_{1.0}V_{0.25-0.45}Te_{0.10-0.16}Nb_{0.15-0.19}O_d$ where d is a number to satisfy the valence of the oxide.

In some preparation methods, the dried catalyst active phase precursor is treated with a peroxide, typically hydrogen peroxide. The hydrogen peroxide treatment may take place at atmospheric pressure and room temperature (e.g. from 15° C. to 30° C.) to about 80° C., in some instances from 35° C. to 75° C. in other instances from 40° C. to 65° C. The hydrogen peroxide may have a concentration from 10 to 30 wt %, in some instances from 15 to 25 wt % in water. The treatment time may range from 1 to 10 hours, in some cases from 2 to 8 hours, in other cases from 4 to 6 hours. The catalyst active phase precursor is treated with the equivalent of from 0.3-2.8, in some embodiments from 0.3-2.5 ml of a 30 wt % solution of aqueous $H_2O_2$ per gram of precursor. The treatment should be in a slurry (e.g. the precursor is at least partially suspended) to provide an even distribution of $H_2O_2$ and to control the temperature rise. For post calcination treatment with $H_2O_2$ there is a sudden delayed violent reaction with $H_2O_2$. This results in an instantaneous reaction which is more controlled and safer.

The treated catalyst precursor is then subject to calcining to produce the active oxidative dehydrogenation catalyst. The treated precursor may be calcined in an inert atmosphere at a temperature from 200° C. to 600° C. for a time from 1 to 20 hours. The purge gases used for calcining are inert gases, including one or more of nitrogen, helium, argon, $CO_2$ (for example high purity >90%), said gases or mixture containing less than 1 vol.-% hydrogen or air, at 200-600° C., or at 300-500° C. The calcining step may take from 1 to 20, in some instances from 5 to 15 in other instances from about 8 to 12 hours, or for example about 10 hours. The resulting mixed oxide catalyst active phase is a friable solid typically insoluble in water. Typically, the calcined product has a bulk density from 1.20 to 1.90 g/cc. This bulk density is based on how much 1.5 ml of pressed and crushed catalyst weighs.

When the peroxide treatment is used, the catalyst active phase may have the formula:

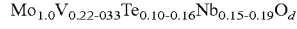

$Mo_{1.0}V_{0.22-0.33}Te_{0.10-0.16}Nb_{0.15-0.19}O_d$ as determined by PIXE where d is a number to satisfy the valence of the oxide.

In some processes, the hydrothermal treatment may be carried out at a controlled low pressure from 10 psi to 190 psi (960 kPa to 1300 kPa). This may be achieved by having a vent to the autoclave and some suitable pressure control means such as a regulator or in some instances a column of a liquid, such as water, through which the vent gasses must escape. In such a process, the duration of the hydrothermal treatment may extend up to 72 hours.

When prepared by this method the catalyst active phase may have the formula:

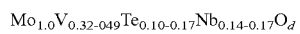

$$Mo_{1.0}V_{0.32-0.49}Te_{0.10-0.17}Nb_{0.14-0.17}O_d$$

where d is a number to satisfy the valence of the oxide.

In some methods, the pressure in the hydrothermal reactor may be reduced even further to a range from 1 to 8 psig (6.89 kPag to 55.1 kPag), or less than 5 psig (34.4 kPag) above atmospheric pressure. Under these conditions the catalyst active phase may have the empirical formula as measured by PIXE:

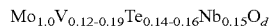

$$Mo_{1.0}V_{0.12-0.19}Te_{0.14-0.16}Nb_{0.15}O_d$$

where d is a number to satisfy the valence of the oxide.

The present disclosure contemplates the use of mixtures or combinations of the above materials.

In accordance with the present disclosure, from 10 to 95, or from weight % of the catalyst active phase is agglomerated (extruded) with from 5 to 90, weight % of $Nb_2O_5$ and optionally from 0 up to 80 weight % of a non-antagonistic binder.

The agglomerated catalyst may be prepared by methods known to those skilled in the art. In one embodiment, the calcined catalyst is suspended in a diluent, typically water and prepared or purchased acidic, neutral or basic suspensions of binder(s) are added to the catalyst suspension in the amounts noted above.

The $Nb_2O_5$ hydrate and optional non-antagonistic binder may be purchased or made as an acidic, neutral or basic paste slurry or suspension containing from about 3 wt % to 90 wt %, in some embodiments 20 wt % to 80 wt % of the $Nb_2O_5$ hydrate or optional non-antagonistic binder, typically from about 40 to 60 wt % of the $Nb_2O_5$ hydrate and optional non-antagonistic binder. The balance of the $Nb_2O_5$ hydrate and optional non-antagonistic binder is a volatile diluent, for example water. Other additives can be present in the $Nb_2O_5$ hydrate or optional non-antagonistic binder solution for improving adhesion to catalytic active phase. The paste, slurry or suspension of the $Nb_2O_5$ hydrate or optional non-antagonistic binder may have a pH from about 0.5 to 12, in some embodiments 3 to 6. The paste, slurry or suspension of the $Nb_2O_5$ hydrate or optional non-antagonistic I binder may be acidified using a conventional acid chosen from hydrochloric acid, hydrobromic acid, hydroiodic acid, perchloric acid, sulfuric, nitric acid, and organic acids and mixtures thereof. The basic paste, slurry or suspension of the $Nb_2O_5$ hydrate or optional non-antagonistic binder may be treated with common bases, for example volatile bases such as lower di $C_{1-6}$ alkyl amines with a pH from 7.5 to 12, in some embodiments from 8 to 10.

In some embodiments, the slurry of hydrated $Nb_2O_5$ in an amount greater than 20 wt % when added to the slurry of catalyst active phase and optional non-antagonistic binder to form a paste, slurry or slip (herein after referred to as slip) acts predominantly as a binder. The slip is prepared without the co-comminution of the catalyst active phase, the $Nb_2O_5$ and optional non-antagonistic binder. The diluent is partially separated from the suspension typically by drying but other means such as filtering or applying a vacuum may be suitable. The content of diluent (water) in the resulting slip is generally reduced to less than 30 wt %, or less than 25 wt %, in some embodiments less 20 wt %. In some embodiments, the blend is heated at temperatures from about 90 to 100° C. at atmospheric pressure. As noted above in some instances a vacuum may be applied resulting a corresponding reduction in temperature to remove the diluent. It is important that the partially dried mixtures is sufficient fluid that it may flow through the extruder under normal operating conditions.

In some embodiments, the slurry of hydrated $Nb_2O_5$ in an amount less than 20 wt %, in some embodiments less than 15 wt %, in further embodiments less than 10 wt %, or for example 8 wt %, when added to the slurry of catalyst active phase and optional non-antagonistic binder to form a paste, slurry or slip (herein after referred to as slip) acts predominantly as a promotor for the agglomerated catalyst. The slip is prepared without the co-comminution of the catalyst and the promotor. The diluent is partially separated from the suspension typically by drying but other means such as filtering or applying a vacuum may be suitable. The content of diluent (water) in the resulting slip is generally reduced to less than 30 wt %, or less than 25 wt %, in some embodiments less 20 wt %. In some embodiments, the blend is heated at temperatures from about 90 to 100° C. at atmospheric pressure. As noted above in some instances a vacuum may be applied resulting a corresponding reduction in temperature to remove the diluent. It is important that the partially dried mixtures is sufficient fluid that it may flow through the extruder under normal operating conditions.

Some non-antagonistic binders include oxides of aluminum such as Boehmite (Al(O)OH), titanium and zirconium. In some embodiments the oxides of aluminum, titanium and zirconium are present in the amount 35-65 wt % based on the weight of the agglomerated catalyst. In some embodiments $ZrO_2$ should not be used in combination with an aluminum based binder. Silica oxides have an antagonistic effect on the agglomerated catalysts and the catalyst active sites. The surface area of the resulting catalyst may be as high as 250 $m^2/g$. Typically use of the non-antagonistic binders in an amount of less than 35 wt %, or less than 20 wt %, have a cumulative surface area less than 35 $m^2/g$ as measured by BET, alternatively, less than 20 $m^2/g$, alternatively, less than 3 $m^2/g$.

To improve the flow properties of the mixture or slip, it may be desired to include one or more flow improving agents and/or extrusion aids in the mixture prior to extrusion. Suitable additives for inclusion in the mixture include cellulose or its derivatives, fatty amines, quaternary ammonium compounds, polyvinyl pyridine, polyvinyl alcohol, sulphoxonium, sulphonium, phosphonium and iodonium compounds, alkylated aromatic compounds, acyclic monocarboxylic acids, fatty acids, sulphonated aromatic compounds, alcohol sulphates, ether alcohol sulphates, sulphated fats and oils, phosphonic acid salts, polyoxyethylene alkylphenols, polyoxyethylene alcohols, polyoxyethylene alkylamines, polyoxyethylene alkylamides, polyacrylamides, polyols and acetylenic glycols. Some additives are sold under the trademarks Nalco and Superfloc.

The compaction pressure in the extruder was adjusted to produce structures with average (side) crush strengths up to 110 N/mm (22.5 lb).

The resulting product (slip) has the consistency of a paste or a thick paste (e.g., mud). The paste is extruded, passing through a cutter into a shaped product such a sphere, rod, including trilobite rods, ring or a saddle and then dried. The particles typically rods may be subject to spheritization to produce spheres having a diameter up to about 5 mm, typically from about 2 to 3 mm.

Growth Agglomeration (Agitation Methods)

Extruded particles may be aggregated with each other in a fluid flowing system. This is usually done in the presence of liquid and binders. The particle size enlargement occurs by coalescence or aggregation (snowballing) based on capillary forces. In a few exceptional cases, the major cohesive force is the van der Waals force. Usually the agglomerates are spherical with diameters between 0.5 and 20 mm. Typical equipment types include drums, cones, pans, paddle mixers and plowshare mixers.

The extruded/aggregated product may have a diameter from about 0.5 to 5 mm, typically from 1.3 to 2.5 mm, desirably from 1.35 to 1.45 mm and a length of up to 8 mm, typically less than 5 mm. The particles may have an aspect ratio from 1 (e.g. a sphere) to 5/1.3.

As the slip passes through the extruder a number of changes occur. The extruder may help to reduce the content of the diluent (e.g. water) in the product. Depending on the pressure in the extruder it will collapse some of the interstitial voids within the slip. As a result the extruded and dried particles may have a having a surface area less than 35 m$^2$/g, alternatively, less than 20 m$^2$/g, alternatively, less than 3.0 m$^2$/g as measured by BET. As a result the agglomerated and dried particles may have a pore volume range from about 0.05 to 0.50 cm3/g. The resulting shaped product is then dried in air at a temperature from about 80° C. to about 150° C., typically less than 120° C., in some embodiments less than 110° C. The dried particulate catalyst is then calcined at a temperature from 300° C. to 600° C., in some embodiments from 350° C. to 500° C. The agglomerated catalyst is calcined for a period of time of not less than 1 hour, typically up to about 4 hours.

The final particle should have a crush strength sufficiently to withstand the operating condition in the ODH reactor. The crush strength may range up to 110 N/mm, in some embodiments 10 N/mm (2.25 lb/mm) or less (e.g. for rods). The resulting agglomerated catalyst may have a pore size distribution less than 4% having pore width size less than 150 Angstroms. Alternatively, resulting agglomerated catalyst may have a cumulative pore volume from 0.02 to 0.20 cm3/g.

Oxidative Dehydrogenation Reaction

In some embodiments, the oxidative dehydrogenation (ODH) process comprises passing a mixed feed of ethane and oxygen at a temperature less than 420° C. in some instances less than 410° C., in some instances less than 400° C., in some instances less than 390° C., in some instances less than 380° C. The catalysts disclosed herein may be used at a gas hourly space velocity of not less than desirably not less than 1500 hr$^{-1}$, or at least 3000 hr$^{-1}$ through one or more fixed beds at a pressure from 0.8 to 1.2 atmospheres. In some embodiments the catalyst of the present disclosure permit the oxidative dehydrogenation reactor operates at temperatures typically from 300° C. to 450° C., in some instances from 330 to 380° C. in some embodiments from 340° C. to 360° C. at a space velocity from 500 hr$^{-1}$ to 3000 hr$^{-1}$.

The outlet pressure from the ODH reactor may be from 105 kPag (15 psig) to 172.3 kPag (25 psig) and the inlet pressure is higher by the pressure drop across the bed which depends on a number of factors including reactor configuration, particle size in the bed and the space velocity. In some embodiments the pressure drop may be below 689 kPag (100 psig), or less than 206.7 kPag (30 psig).

The residence time of one or more alkanes, typically $C_{2-4}$ alkanes, in the reactor is from 0.002 to 20 seconds.

The feed to the oxidative dehydrogenation reactor includes oxygen in an amount above the upper explosive/flammability limit. For example for ethane oxidative dehydrogenation, in a feed stream essentially comprising oxygen and ethane, typically the oxygen will be present in an amount of not less than about 16 mole %, or about 18 mole %, for example from about 22 to 27 mole %, or 23 to 26 mole %. In some embodiments it is desirable not to have too great an excess of oxygen as this may reduce selectivity arising from combustion of feed or final products. Additionally, too high an excess of oxygen in the feed stream may require additional separation steps at the downstream end of the reaction. In some circumstances the feed stream may be diluted with a feed gas having a low reactivity such as nitrogen, argon, helium $CO_2$, CO, steam.

In some embodiments, the percentage of alkane may be up to 40 mole %. For instances where the mixture of gases prior to ODH comprises 25 mole % oxygen and 40 mole % alkane, the balance must be made up with an inert diluent, such as nitrogen, carbon dioxide, or steam. The inert diluent should exist in the gaseous state in the conditions within the reactor and should not increase the flammability of the hydrocarbon added to the reactor, characteristics that a skilled worker would understand when deciding on which inert diluent to employ.

The goal is for 100% conversion, of alkane with minimal unreacted alkane and oxygen leaving the ODH reactor, and a minimum production of carbon monoxide or carbon dioxide. In an embodiment of the invention, the product stream leaving the ODH reactor contains less than 5% unreacted lower alkane, or less than 2.5%, or less than 1%. In another embodiment of the invention, the product stream leaving the ODH reactor contains less than 2% oxygen, or less than 1.5% oxygen, or less than 1% oxygen.

In a further embodiment of the oxidative dehydrogenation process, the amount of binder in the extruded catalyst is increased within range from 5 to 50 wt % and the gas flow rate through the catalyst bed is increased by a proportional amount (e.g. the amount of binder is increased by 10% the gas flow rate is increased by up to 10%) while maintaining the bed temperature less than 420° C., or less than 395° C., or less than 285° C., and maintaining the selectivity within ±3%.

This improves the economics of the reaction akin to increasing the productivity.

The present invention will now be illustrated by the following non limiting examples.

Example 1

A base catalyst was prepared using a conventional hydrothermal process as described above. The calcined catalyst had the empirical formula:

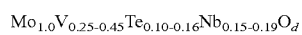

where d is a number to satisfy the valence of the oxide.

The catalyst was dispersed in water and mixed with various inorganic oxides both basic, acidic and neutral. The compositions are listed in Table 1 below.

TABLE 1

| Binder Component | Concentration (wt % in H$_2$O) | Specific Gravity | Surface area (m$^2$/g) | pH | Notes |
|---|---|---|---|---|---|
| Nb$_2$O$_5$ xH$_2$O | NA | Not given | Not given | 0-7 | |
| SiO$_2$ | 140 | | | 4-7 | Deionized no counter ion |
| AlO(OH) | N/A | Not given | 320 | N/A | Boehmite Alumina |

TABLE 2

| Sample # | Catalyst Code | Temperature at 25% Conversion (° C.) | Selectivity at 25% Conversion |
|---|---|---|---|
| Sample 1 | Baseline Catalyst | 367 | 98 |
| Sample 2 | Active Phase + 1M HNO3 | 366 | 97 |
| Sample 3 | Active Phase + 8% deionized, neutral SiO2 binder | 372 | 97 |
| Sample 4 | Active Phase + 8% acidic SiO2 binder) | 385 | 97 |
| Sample 5 | Active Phase + 8% basic SiO2 binder) | 374 | 97 |
| Sample 6 | Active Phase + 8% Nb$_2$O$_5$ + HNO$_3$ (promotor) | 351 | 97 |
| Sample 7 | Active Phase + 15% neutral Nb$_2$O$_5$ (binder) | 386 | 96 |
| Sample 8 | Active Phase + 20% neutral Nb$_2$O$_5$ (binder) | 382 | 96 |
| Sample 9 | Active Phase + 40% neutral Nb$_2$O$_5$ (binder) | 388 | 96 |
| Sample 10 | Active Phase + 60% neutral Nb$_2$O$_5$ (binder) | 371 | 96 |
| Sample 11 | Active Phase + 8% Nb$_2$O$_5$ (promotor) | 356 | 97 |
| Sample 12 | Active Phase + 8% Nb$_2$O$_5$ + 60% AlO(OH) (promotor) | 350 | 95 |
| Sample 13 | Active Phase + 8% Nb$_2$O$_5$ + 60% SiO$_2$ (binder) | 412 | 94 |

TABLE 3

| Catalyst | Feed Gas Flow (sscm) | Temperature at 25% Conversion (° C.) | Selectivity to Ethylene (%) |
|---|---|---|---|
| Baseline ODH Catalyst (I) | 140 (no compensation) | 367 | 98 |
| (I) + 8% SiO$_2$ A | a) 140 | 385 | 97 |
| | b) 151 (8% increase) | 390 | 98 |
| (I) + 8% SiO B | a) 140 | 374 | 97 |
| | b) 151 (8% increase) | 380 | 97 |
| (I) + 8% Nb$_2$O$_5$ | a) 140 | 356 | 97 |
| | b) 151 (8% increase) | 360 | 97 |
| (I) + 20% Nb$_2$O$_5$ | a) 140 | 389 | 96 |
| | b) 168 (20% increase) | 382 | 96 |
| (I) + 40% Nb$_2$O$_5$ | a) 140 | 371 | 96 |
| | b) 196 (40% increase) | 388 | 96 |

The amount of binder (weight %) based on elemental weight percentage composition of the solution is indicated in the table. The resulting slurry was extruded or spheritized as above, dried 90-100° C. and re-calcined in air at 350-500° C. The agglomerated particles were tested in a lab scale dehydrogenation reactor. Where ethane and oxygen in about a 1:1 molar ratio were passed through a fixed bed at the same rate of flow of the starting feedstock. The temperature at which 25% conversion occurred and the selectivity at that conversion were recorded.

The results support the following conclusions.
1. SiO$_2$ is an antagonist to the catalyst for the oxidative dehydrogenation of ethylene (Samples 3, 4, 5 and 13). The temperature at which there is 25% conversion of ethane to ethylene goes up.
2. The addition of only an acid to the catalyst has virtually no effect (Samples 1 and 3).
3. The addition of Nb$_2$O$_5$ hydrate in amounts less than about 10 wt % acts as a promotor/binder for oxidative dehydrogenation catalysts (active phase) significantly reduces the temperature at 25% conversion and maintains a high selectivity.
4. Example 6 and 12 show that the presence of the Boehmite has virtually no effect on the promoting effect of Nb$_2$O$_5$ hydrate. The use of less than 15 wt % of Nb$_2$O$_5$ hydrate the balance a neutral binder acts as a promoter.
5. Nb$_2$O$_5$ hydrate when present in the support in amounts greater than 15 wt % acts as a binder and doesn't promote the catalyst.

What is claimed is:

1. An agglomerated catalyst, wherein the agglomerated catalyst is prepared from:
   forming an aqueous slurry or paste comprising 10 wt. % to 95 wt. % of a catalyst active phase of the formula:

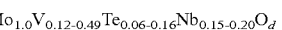
   $$Mo_{1.0}V_{0.12-0.49}Te_{0.06-0.16}Nb_{0.15-0.20}O_d$$

wherein d is a number to satisfy the valence of the oxide; and
   adding to the aqueous slurry or paste 5 wt. % to 90 wt. % of a binder of Nb$_2$O$_5$ hydrate, and adding to the aqueous slurry or paste optionally up to 80% wt % of a non-antagonistic binder; reducing the water content of the resulting slurry or paste to less than 30 wt %; extruding the water reduced slurry or paste to form particles; drying the particles in an oxygen containing atmosphere at temperature from 90 to 115° C.; calcining the resulting dried particles at temperature up to 600° C.; wherein the agglomerated catalyst has a pore size distribution so that less than 40% of the pores having a pore width size less than 200 Angstroms and 60% of the pores having a pore width size greater than 200 Angstroms.

2. The agglomerated catalyst according to claim 1, having a cumulative surface area less than 10 m$^2$/g as measured by BET and prepared from comprising less than 35 wt. % of a non-antagonistic binder.

3. The agglomerated catalyst according to claim 2, having a cumulative pore volume from 0.020 to 0.20 cm$^3$/g.

4. The agglomerated catalyst according to claim 2, in the shape of a sphere, rod, ring, or a saddle having a size from about 1.3 mm to about 5 mm.

5. The agglomerated catalyst according to claim 4, wherein the Nb$_2$O$_5$ hydrate is acidified.

6. The agglomerated catalyst according to claim 4, wherein the Nb$_2$O$_5$ hydrate is treated with a base.

7. The agglomerated catalyst according to claim 6, in the shape of rods having an aspect ratio from 1 to 5/1.3 having a crush strength up to 110 N/mm.

8. The agglomerated catalyst according to claim 6, in the shape of spheres having a crush strength up to 110 N/mm.

9. The agglomerated catalyst according to claim 1, wherein the agglomerated catalyst is prepared from at least 5 wt. % to 15 wt. % of Nb$_2$O$_5$ hydrate.

10. The agglomerated catalyst according to claim 1, wherein the agglomerated catalyst is prepared from at least 15 wt. % to 90 wt. % of $Nb_2O_5$ hydrate.

11. The agglomerated catalyst according to claim 4, wherein the catalyst active phase has the empirical formula:

$$Mo_{1.0}V_{0.25-0.38}Te_{0.10-0.16}Nb_{0.15-0.19}O_d$$

where d is a number to satisfy the valence of the oxide.

12. The agglomerated catalyst according to claim 4, wherein the catalyst active phase has the empirical formula as determined by PIXE:

$$Mo_{1.0}V_{0.22-0.33}Te_{0.10-0.16}Nb_{0.15-0.19}O_d$$

where d is a number to satisfy the valence of the oxide.

13. The agglomerated catalyst according to claim 4, wherein the catalyst active phase has the empirical formula as measured by PIXE:

$$Mo_{1.0}V_{0.12-0.19}Te_{0.14-0.16}Nb_{0.15}O_d$$

where d is a number to satisfy the valence of the oxide.

14. The agglomerated catalyst according to claim 4, wherein the catalyst active phase has the empirical formula as measured by PIXE:

$$Mo_{1.0}V_{0.17-0.20}Te_{0.06-0.07}Nb_{0.19-0.20}O_d$$

where d is a number to satisfy the valence of the oxide.

15. The agglomerated catalyst according to claim 4, wherein the catalyst active phase has the empirical formula as measured by PIXE:

$$Mo_{1.0}V_{0.12-0.19}Te_{0.14-0.16}Nb_{0.15}O_d$$

where d is a number to satisfy the valence of the oxide.

16. The agglomerated catalyst according to claim 15, wherein the non-antagonistic binder is chosen from an aluminum oxide, a titanium oxide, a zirconium oxide, or a combination thereof.

17. The agglomerated catalyst according to claim 16, wherein the non-antagonistic binder is present in the amount of 35 wt. % to 65 wt. % when preparing the agglomerated catalyst and the agglomerated catalyst has a surface area up to 250 $m^2/g$.

18. The agglomerated catalyst according to 16, wherein the aluminum oxide is Boehmite (Al(O)OH).

19. The agglomerated catalyst according to claim 16, wherein the non-antagonistic binder is titanium oxide.

20. The agglomerated catalyst according to claim 16, wherein the non-antagonistic binder is zirconium oxide.

* * * * *